United States Patent [19]

Hood, Jr.

[11] Patent Number: 5,746,203

[45] Date of Patent: May 5, 1998

[54] FAILSAFE SUPERVISOR SYSTEM FOR A PATIENT MONITOR

[75] Inventor: Rush W. Hood, Jr., Tampa, Fla.

[73] Assignee: Johnson & Johnson Medical, Inc., New Brunswick, N.J.

[21] Appl. No.: 721,140

[22] Filed: Sep. 26, 1996

[51] Int. Cl.[6] ........................................ A61B 5/00
[52] U.S. Cl. .............................. 128/630; 395/182.22
[58] Field of Search ........................ 128/630; 607/16; 395/182.22, 185.08

[56] References Cited

U.S. PATENT DOCUMENTS

| | | | |
|---|---|---|---|
| 4,365,290 | 12/1982 | Nelms et al. | 607/16 |
| 4,627,060 | 12/1986 | Huang et al. | 395/185.08 |
| 5,056,092 | 10/1991 | Bruner | 395/182.22 |
| 5,068,853 | 11/1991 | Soma et al. | 395/182.22 |

*Primary Examiner*—Jennifer Bahr
*Assistant Examiner*—Eric F. Winakur
*Attorney, Agent, or Firm*—Woodcock Washburn Kurtz Mackiewicz & Norris LLP

[57] ABSTRACT

A failsafe supervisor system for a patient monitor which integrates the functions of coordinating the turning on/off of the patient monitor with the user and the system software, alerting the operator in the event the patient monitor turns off due to a power failure, and alerting the operator to improper operation of the patient monitor system's processor hardware or software. Upon detection of such unexpected changes of state or malfunctions during operation of the patient monitor, the patient monitor is powered down in a failsafe manner to a safe state. Additionally, the failsafe supervisor system optionally allows the operator to select a service mode when turning on the monitor, thereby facilitating testing. The entire failsafe supervisor system is preferably implemented in a small one-chip microcontroller so that it can be readily incorporated into the patient monitor's microprocessor control system.

7 Claims, 5 Drawing Sheets

FAILSAFE PROCESSOR STATE DIAGRAM

FAILSAFE PROCESSOR STATE DIAGRAM WITH SERVICE MODE

FAILSAFE SUPERVISOR SYSTEM FOR A PATIENT MONITOR

BACKGROUND OF THE INVENTION

1. Field of the Invention

The present invention relates to a failsafe supervisor system for a patient monitor, and more particularly, to a failsafe supervisor system which controls the application of power to a patient monitor, alerts the operator to unexpected changes of power state or of malfunctions, and powers down the patient monitor to a safe state when such changes or malfunctions are detected.

2. Brief Description of the Prior Art

Various protection systems, such as those implemented with watchdog timers, have been used in patient monitors in the prior art to detect malfunctions and to safely power down the patient monitor. However, protection systems connected with particular functions, such as the turning on and turning off of the patient monitor, as well as alerting the operator to monitor failures, have been developed in an ad hoc fashion. No consistent, failsafe, power up and power down operation has been used in prior art systems.

In addition, when the patient monitor switches off for any reason other than deliberate operator action (such as the timing out of a watchdog timer, power failure, and the like), the operator must be alerted. However, to date, this action has not been coordinated with the failsafe powering up and powering down of the patient monitor.

Accordingly, it is desired to develop a failsafe supervisor control system for a patient monitor which not only controls the powering up and powering down of a patient monitor during normal operation, but which also alerts the operator of unexpected changes of state or of malfunctions and powers down the patient monitor under such error conditions. The present invention has been designed to meet these needs.

SUMMARY OF THE INVENTION

The present invention relates to a failsafe supervisor system for a patient monitor which meets the above-mentioned needs in the prior art. The failsafe supervisor system of the invention meets such needs by integrating the functions of coordinating the turning on/off of the patient monitor with the user and the system software, alerting the operator in the event the patient monitor turns off due to a power failure, and alerting the operator to improper operation of the patient monitor system's processor hardware or software. Upon detection of such unexpected changes of state or malfunctions during operation of the patient monitor, the patient monitor is powered down in a failsafe manner to a safe state. Additionally, the failsafe supervisor system of the invention optionally allows the operator to select a service mode when turning on the monitor, thereby facilitating testing. The entire failsafe supervisor system of the invention is preferably implemented in a small one-chip microcontroller so that it can be readily incorporated into the patient monitor's microprocessor control system.

A preferred embodiment of a patient monitor in accordance with the invention monitors the on/off state of a patient monitor and failure signals from the microprocessor control system to power down the patient monitor in a failsafe manner when unexpected changes of state or malfunctions are detected. In particular, the patient monitor of the invention collects parameter data related to physiological parameters of a patient and displays the parameter data on a display. For this purpose, the patient monitor comprises means for collecting the parameter data, parameter processing means for processing the parameter data and displaying the processed parameter data on the display and for providing watchdog pulses indicating at least whether the collecting means and the parameter processing means are operating properly, a power supply for selectively providing power to the display, the collecting means, and the parameter processing means upon receipt of a power up or power down signal, an alarm which sounds when upon receipt of an error signal, and an on/off button for selectively turning on/off the patient monitor. However, the patient monitor of the invention is particularly characterized by failsafe supervisor processing means responsive to the on/off button for selectively providing the power up or the power down signals to the power supply and to the watchdog pulses for generating the error signal to sound the alarm when a watchdog pulse is not received by the failsafe supervisor processing means in a predetermined period of time.

The failsafe supervisor processing means is preferably powered by a backup battery at least when the power supply is turned off. A select knob may also be provided as an alternative way to turn on/off the patient monitor. Generally, the select knob permits the operator to select which parameter data the collecting means is to collect. However, in a preferred embodiment, when the select knob is pressed at the same time the on/off button is depressed, the operator may cause the patient monitor to enter a service mode upon power up of the patient monitor.

During operation, the failsafe supervisor processing means of the invention sends an off request to the parameter processing means to cause the parameter processing means to cease its parameter processing in a failsafe manner prior to sending the power down signal to the power supply upon depression of the on/off button while the patient monitor is in an on state.

A plurality of timers also may be implemented in the failsafe supervisor processing means to provide additional time-out functions. For example, a forced-off timer may start counting when the on/off button is depressed while the patient monitor is in an on state. If said forced-off timer reaches a predetermined count before the on/off button is released, the patient monitor is powered down in a failsafe manner irrespective of the status of any parameter processing by the parameter processing means. On the other hand, when a watchdog pulse is not received by the failsafe supervisor processing means in the predetermined period of time and the alarm is sounded, the failsafe supervisor processing means may start a failsafe off timer which causes the power down signal to be sent to the power supply after a power down time interval in the event no action is taken by the operator during the power down time interval in response to the alarm. Similarly, the failsafe supervisor processing means may start an alarm timer which turns off the alarm after an alarm time interval in the event no action is taken by the operator during the alarm time interval to turn off the alarm.

BRIEF DESCRIPTION OF THE DRAWINGS

The objects and advantages of the invention will become more apparent and more readily appreciated from the following detailed description of presently preferred exemplary embodiments of the invention taken in conjunction with the accompanying drawings of which.

DETAILED DESCRIPTION OF PRESENTLY PREFERRED EMBODIMENTS

A failsafe supervisor system with the above-mentioned beneficial features in accordance with a presently preferred exemplary embodiment of the invention will be described below with reference to FIGS. 1-5. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

The present invention relates to a failsafe supervisor system which provides for the safe operation of a patient monitor so as to minimize the likelihood of harm to the patient when a hardware or software error is detected in the patient monitor and when the patient monitor ceases monitoring during use, and which provides for a consistent, failsafe, power up and power down operation for the patient monitor. As used herein, a "failsafe" system is a system which places the monitor in a state which is non-hazardous to the patient or operator when an invalid state is detected. For example, in the event that an invalid state is detected in the main processor's control logic, the "failsafe" system places the monitor in a known safe state, and no data is processed until the patient monitor is returned to normal through a hardware reset or through cycling of the power. A preferred embodiment of a patient monitor which implements such a failsafe supervisor system in accordance with the invention is illustrated in FIG. 1.

Figure 1:
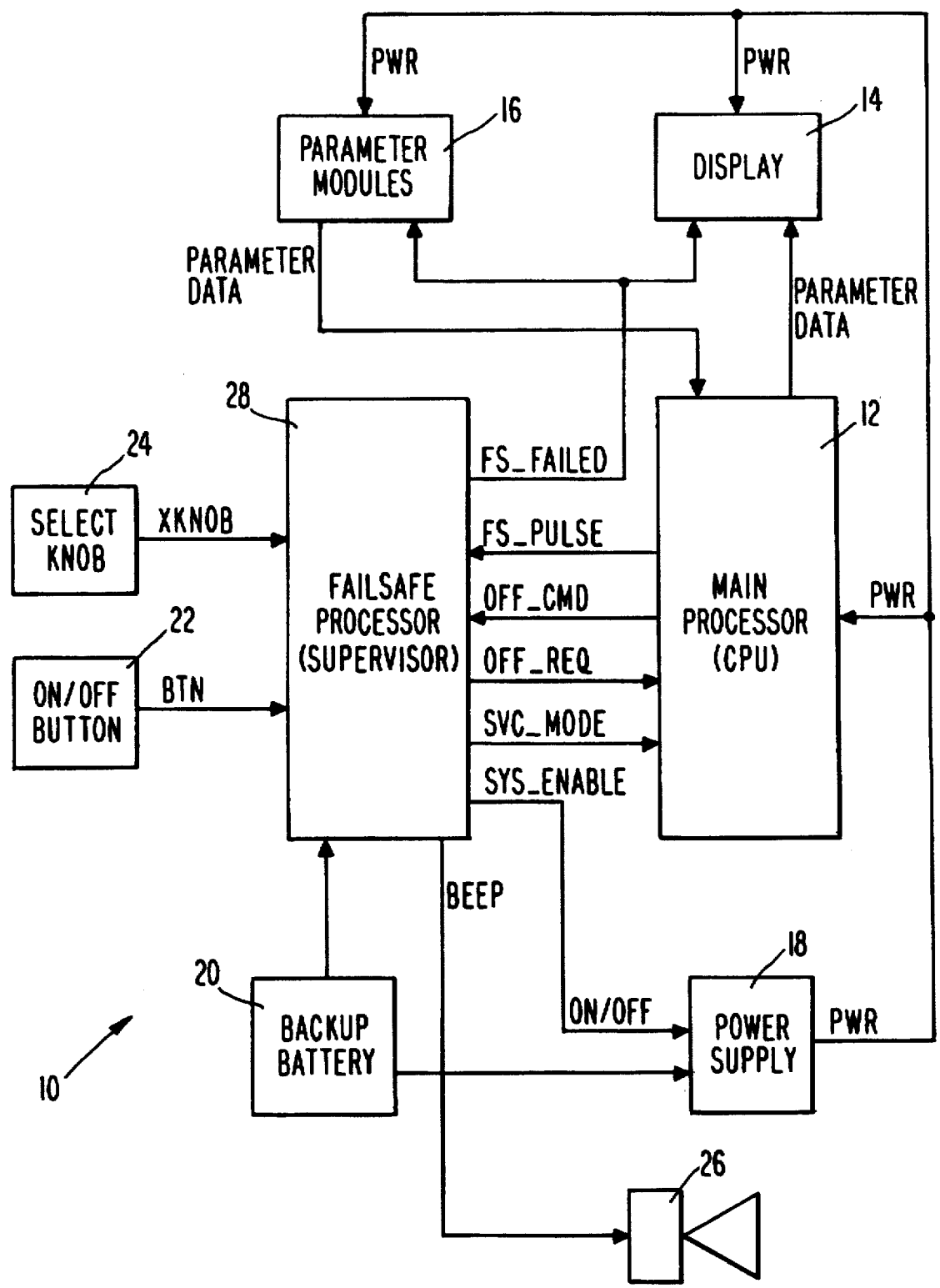
FIG. 1 illustrates a schematic diagram of a patient monitor with a failsafe supervisor system in accordance with a preferred embodiment of the invention.

FIG. 1 illustrates a simplified block diagram of a modular patient monitor, such as the DINAMAP™ MPS Select Monitor, available from Johnson & Johnson Medical Inc., which implements a failsafe supervisor system in accordance with the invention. As shown in FIG. 1, the patient monitor 10 includes a main processor 12, a display 14, and one or more monitor modules 16. Monitor modules 16 are separate parameter modules which mate with the main processor 12 during use to selectively collect patient data such as $CO_2$ exhaled by the patient, the patient's heart rate, the patient's blood pressure (invasive or noninvasive), the patient's temperature, the patient's electrocardiogram, the oxygen saturation ($SpO_2$) of the patient's arterial blood, and/or the patient's respiration rate. Main processor 12, display 14, and modules 16 receive power from a power supply 18 or, in the event of a power failure, from a backup battery 20 when on/off button 22 is depressed. Alternatively, power may be applied to the components in response to actuation of a select knob 24 used to select which of the modules 16 is to display its collected patient data on display 14. During operation, main processor 12 implements one or more watchdog timer circuits which monitor system hardware and software operation to cause an alarm 26 to sound in the event such an error is detected. Finally, a failsafe processor 28 designed in accordance with the invention is provided to control the power up/down of the patient monitor 10 in response to input from on/off button 22 and/or select knob 24 and to control the operation of the alarm 26 when an error is detected by the main processor 12 or the patient monitor 10 attempts to power down without operator selection.

In accordance with a preferred embodiment of the invention, failsafe processor 28 performs the functions of powering on/off the patient monitor 10 in a manner which coordinates the operator's action of depressing the on/off button 22 with the system software's state, powering an alarm 26 which alerts the operator in the event the patient monitor 10 is turned off due to a system failure or in the event that improper operation of the patient monitor's hardware or software is detected, and selectively allowing the operator to select a service mode when turning on the patient monitor 10. As shown in FIG. 1, failsafe processor 28 is responsive to several inputs, including an on/off signal (BTN) from on/off button 22, a select signal (XKNOB) from select knob 24, and an off command (OFF_CMD) and failsafe pulses (FS_PULSE) from main processor 12. The failsafe processor 28 processes these inputs and provides several control outputs, including a power control (SYS_ENABLE) output for controlling the state of the main power supply 18 to turn the patient monitor 10 on and off, an off request (OFF_REQ) which informs the main processor 12 that the operator has pressed the on/off button while the patient monitor 10 is on, a failure control (FS_FAILED) output which informs the hardware of the patient monitor 10 that a failsafe watchdog timer has timed out and that the hardware should power down into a safe state, an alarm activation (BEEP) signal which activates the alarm 26 when an error is detected, and, if desirable, a service mode (SVC_MODE) signal which instructs the main processor 12 that the operator has selected the service mode.

On/off push button 22 provides a signal (BTN) to the failsafe processor 28 indicating that the on/off push-button 22 has been pressed to turn on the patient monitor 10 or to request that the software of the main processor 12 turn off the patient monitor 10. When the patient monitor is off, pressing on/off push-button 22 turns on the system power, while when the patient monitor 10 is on, pressing the on/off push-button 22 signals a request to main processor 12 that the patient monitor 10 is to be powered down. Software of the main processor 12 may request confirmation from the operator before issuing a turn-off command (OFF_CMD) to the failsafe processor 28. The OFF_CMD from the main processor 12 instructs the failsafe processor 28 to turn off the system power by issuing an appropriate SYS_ENABLE signal to the power supply 18. On the other hand, if the on/off push-button 22 is depressed when the patient monitor is on and the alarm 26 is sounding, actuation of the on/off push-button 22 will cause the patient monitor 10 to be turned off and the alarm 26 to be silenced. Additionally, if the on/off push-button 22 is depressed and held in for a predetermined duration (such as 5 seconds) while the patient monitor 10 is on, the patient monitor 10 is immediately turned off regardless of the state of the software. This override feature allows recovery from system failures which prevent the software from switching off the patient monitor 10.

In a preferred embodiment of the patient monitor 10, the operator may also power on the patient monitor 10 by pressing a push-button built into select knob 24 which is otherwise used to permit the operator to navigate through the system options depending upon which parameter modules 16 are plugged into the patient monitor 10 at any given time.

On the other hand, if the select knob 24 and the on/off push-button 22 are depressed at the same time, the operator may enter a service mode for running diagnostics, performing software updates, and the like on the patient monitor 10.

The patient monitor 10 preferably implements a failsafe system using watchdog timers in the main processor 12 which provide periodic pulses FS_PULSE to the failsafe processor 28 at a rate greater than a predetermined rate when the patient monitor 10 is operating properly. Since the failure of the FS_PULSE signal to appear on schedule is generally caused by a malfunction or loss of power to the patient monitor 10, if the pulses FS_PULSE are interrupted for any reason, and hence not detected by the failsafe processor 28 for longer than a time period set by the predetermined rate, the failsafe processor 28 issues a BEEP signal to the alarm 26 to sound the alarm and issues a SYS_ENABLE signal to power supply 18 to turn off the system power (PWR). An FS_FAILED signal is also supplied to the respective hardware devices of the patient monitor 10. For example, when powering down in a failsafe manner, the display 14 is blanked, the alarm 26 is activated, input devices are inactivated, and communications to/from the main processor 12 are disabled. Failsafe processor 28 is powered by backup battery 20 so that it is not powered down and remains in operation.

The operation of the supervisor software of failsafe processor 28 will now be described with respect to FIGS. 2-5.

Figure 2:
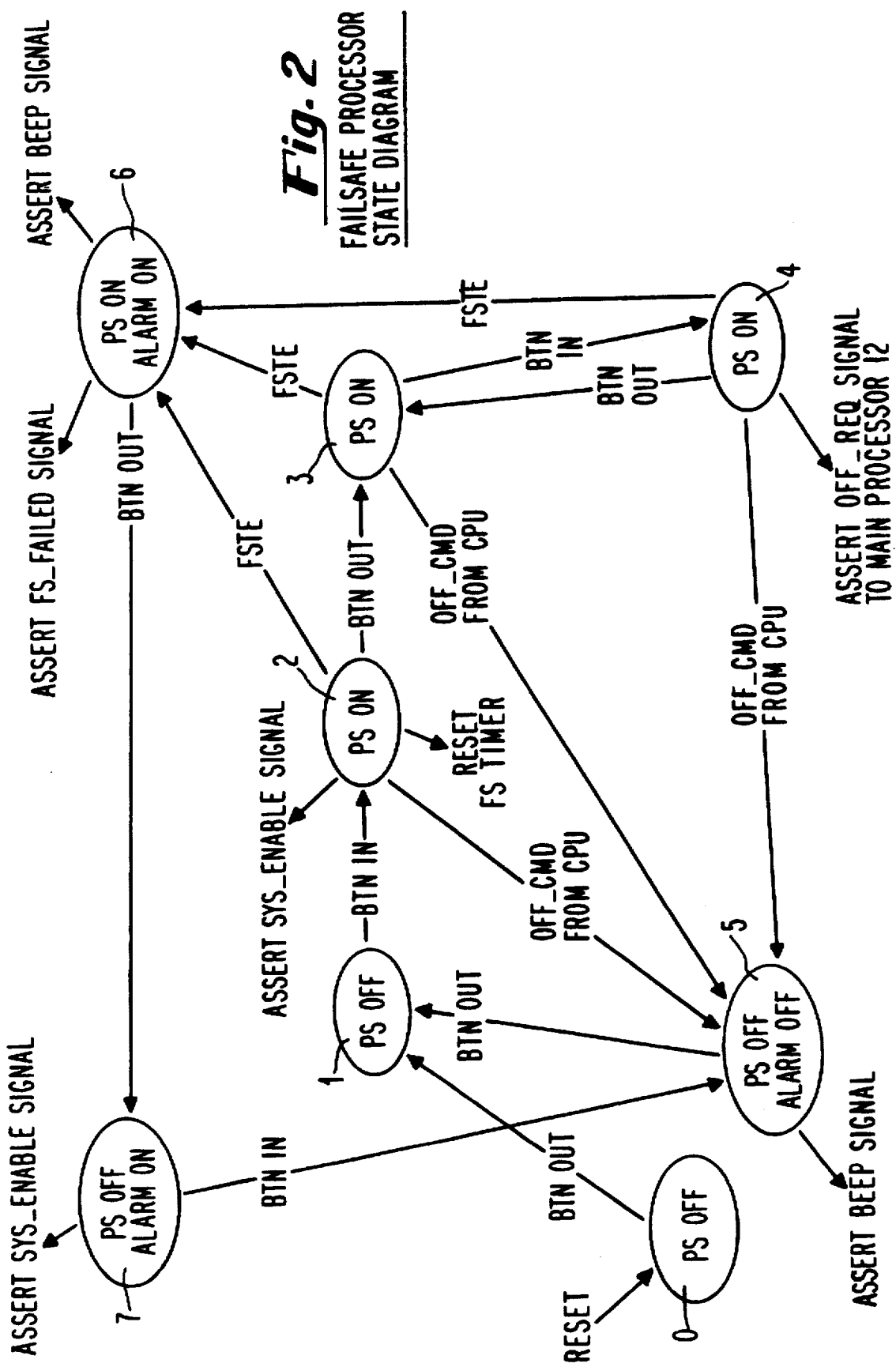
FIG. 2 illustrates an embodiment of a state diagram of the failsafe supervisor system of the invention.

FIG. 2 illustrates a preferred embodiment of a state diagram of the supervisor software of the failsafe processor 28. As illustrated, the supervisor software of the failsafe processor 28 may assume one of eight different states depending upon the inputs received. The supervisor software begins operation in state 0, where the power supply 18 is off. State 0 is entered at initial startup (when the battery is installed) or in the event of a failure in the supervisor hardware or software, in which case a hardware "reset" is received. Assuming the on/off push-button 22 is released (BTN_OUT), the supervisor software moves to state 1, which is the normal resting off state. The power supply 18 is off and the alarm 26 is silent.

Once in the normal off state (state 1), depressing the on/off push-button 22 will cause the supervisor software to move to intermediate state 2, turning on the power to the patient monitor 10 by asserting the SYS_ENABLE signal. When the on/off push-button 22 is subsequently released, the supervisor software moves to state 3, the normal resting on state. Also, when the patient monitor 10 switches on at entry to state 2, the failsafe timer is reset. The failsafe timer is additionally reset each time a FS_PULSE is received from the main processor 12. When in state 3, the normal on state, depressing the on/off push-button 22 causes the supervisor software to proceed to state 4, signaling the main processor 12 via OFF_REQ that the operator wishes to turn off the patient monitor 10. Releasing the on/off push-button 22 returns the supervisor software to state 3. Repeated presses and releases of the on/off push-button 22 cycles the supervisor software between states 3 and 4, but if the software does not issue an OFF_CMD, the supervisor software state is not further affected. The main processor 12, having received the off request, may either directly or after confirmation with the operator issue an OFF_CMD to the supervisor software. An OFF_CMD, whether received in state 2, 3, or 4, moves the supervisor software to state 5, an intermediate off state. The supervisor software proceeds to state 1, the normal off state, when the on/off push-button 22 is not depressed.

The state of the failsafe timer is monitored during states 2, 3, and 4, the normal on states, and if the failsafe timer counts to a preset limit (i.e., it is not reset soon enough), the supervisor software moves to intermediate state 6, sounding the alarm 26 by asserting the BEEP signal and asserting the FS_FAILED signal to the patient monitor's hardware. If the on/off push-button 22 is released at state 6, the supervisor software moves to state 7, continuing the alarm 26. In state 7, the power is turned off by sending a SYS_ENABLE signal of a different state to power supply 18. Once the operator depresses the on/off push-button 22, the supervisor software then proceeds to state 5, the intermediate off state, where the alarm 26 is silenced by asserting a BEEP signal of a different state. Upon release of the on/off push-button 22, the supervisor software then proceeds to state 1, the normal off state, as described above.

Figure 3:
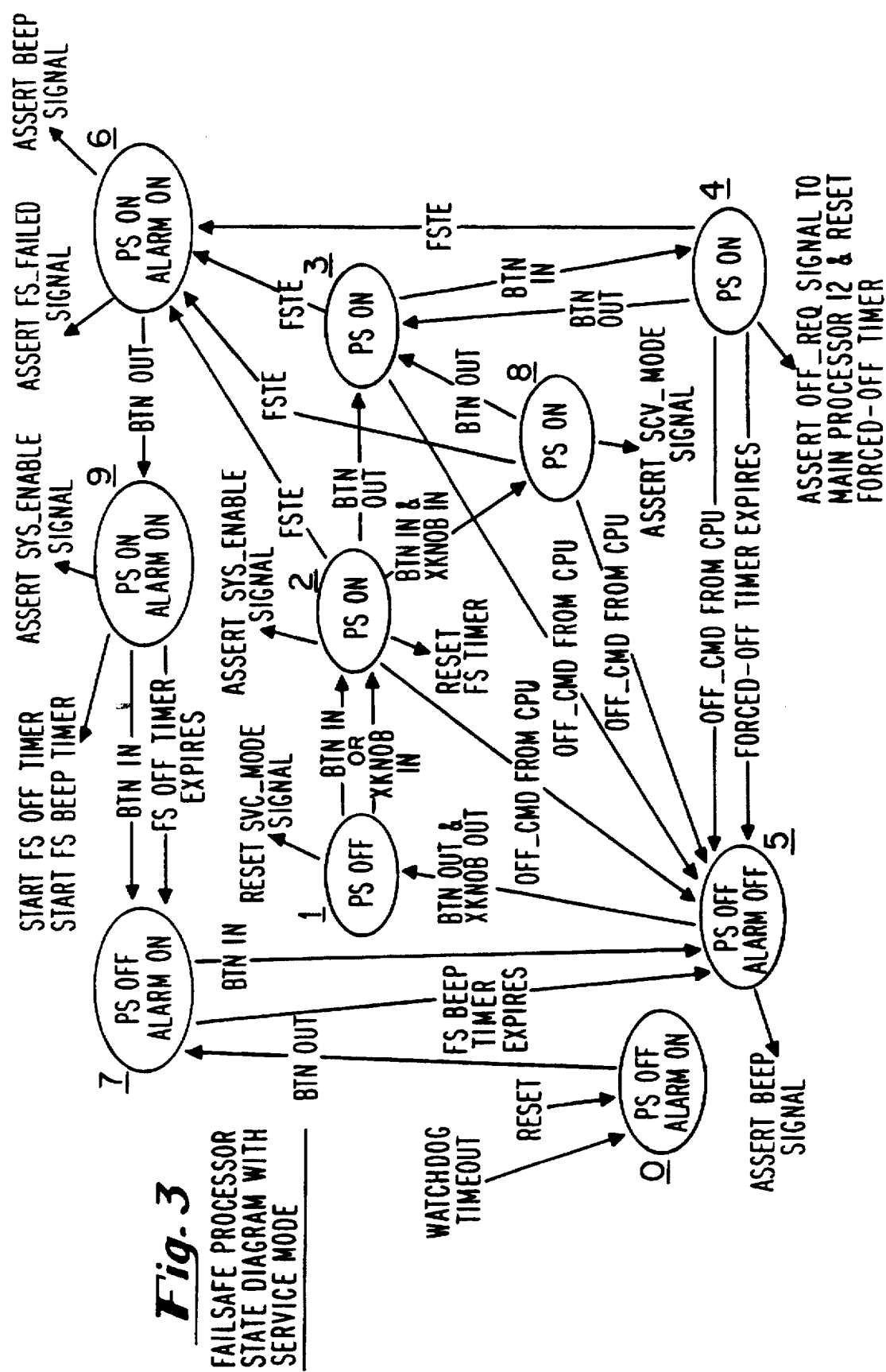
FIG. 3 illustrates a currently preferred embodiment of a state diagram of the failsafe supervisor system of the invention further equipped to provide additional functions.

FIG. 3 illustrates an alternative, more detailed embodiment of a state diagram of the failsafe supervisor system of the invention further equipped to provide a service mode and other functions. As illustrated, the supervisor software of the failsafe processor 28 in this embodiment may assume one of ten different states depending upon the inputs received. The supervisor software begins operation in state 0, where the alarm 26 begins to sound and the power supply 18 is off. State 0 is entered only at initial startup (when the battery is installed) or in the event of a failure in the supervisor hardware or software, in which case the watchdog timer times out or a hardware "reset" is received. Assuming the on/off push-button 22 is released (BTN_OUT), the supervisor software moves to state 7 and waits for the operator to acknowledge the startup alarm by depressing the on/off push-button 22. When the operator depresses the on/off push-button 22, the supervisor software moves to state 5, where a BEEP signal is asserted to silence the startup alarm. Alternatively, the startup alarm will silence and the supervisor software will proceed to state 5 after a failsafe beep timer expires after a delay of, for example, 5 minutes. When the operator releases the on/off push-button 22 and the select knob 24 is out, the supervisor software proceeds to state 1, which is the normal resting off state. The power supply 18 is off and the alarm 26 is silent.

Once in the normal off state (state 1), depressing the on/off button 22 or the select knob 24 will cause the supervisor software to move to intermediate state 2, turning on the power to the patient monitor 10 by asserting the SYS_ENABLE signal. When the on/off button 22 or select knob 24 is subsequently released, the supervisor software moves to state 3, the normal resting on state. Also, when the patient monitor 10 switches on at entry to state 2, the failsafe timer is reset. The failsafe timer is additionally reset each time a FS_PULSE is received from the main processor 12.

When in state 3, the normal on state, depressing the on/off push-button 22 causes the supervisor software to proceed to state 4, signalling the main processor 12 via OFF_REQ that the operator wishes to turn off the patient monitor 10. Releasing the on/off push-button 22 returns the supervisor software to state 3. The main processor 12, having received the off request, may either directly or after confirmation with the operator issue an OFF_CMD to the supervisor software. An OFF$_{13}$ CMD, whether received in state 2, 3, or 4, moves the supervisor software to state 5, an intermediate off state. The supervisor software proceeds to state 1, the normal off state, when neither the on/off push-button 22 nor select knob 24 are depressed. Repeated presses and releases of the on/off push-button 22 cycles the supervisor software between states 3 and 4, but if the software does not issue an OFF_CMD, the supervisor software state is not further affected unless the on/off push-button 22 is held in, thereby keeping the supervisor software in state 4 for a longer time interval. This leads to a "forced-off" turn off method in which the operator can force the patient monitor 10 off by holding the on/off push-button 22 for an extended time (e.g., 5 seconds). Thus, if, for some reason, the patient monitor's software will not respond to the off request and the failsafe timer continues to be reset, the operator can force the patient monitor 10 to turn off. In the forced-off method, when the supervisor software enters state 4, a forced-off timer is reset, and when the supervisor software remains in state 4 for the extended time, the forced off timer expires and the superior software transitions to state 5 to turn off the patient monitor 10.

The supervisor software embodiment of FIG. 3 preferably implements a service mode which allows the operator to service the patient monitor, perform software updates, and the like. As described above, if the patient monitor 10 is off and the on/off push-button 22 is depressed and held, the patient monitor 10 will power up and the supervisor software will be in state 2. If, at this time, the select knob 24 is also pushed, the supervisor software enters state 8, asserting the SVC_MODE signal. This alerts the main processor 12 to enter service mode. When the operator subsequently releases the on/off push-button 22, the supervisor software enters state 3, the normal on state. On the other hand, if an OFF_CMD is received from the main processor 12 while the supervisor software is in state 8, the supervisor software proceeds to state 5, the intermediate off position as noted above. When the on/off push-button 22 or the select knob 24 is released, the supervisor software proceeds to resting off state 1, and the SVC_MODE signal is reset.

The state of the failsafe timer is monitored during states 2, 3, 4, and 8, the normal on states, and if the failsafe timer counts to a preset limit (i.e., it is not reset soon enough), the supervisor software moves to intermediate state 6, sounding the alarm 26 by asserting the BEEP signal and asserting the FS_FAILED signal to the patient monitor's hardware. If the on/off push-button 22 is released at state 6, the supervisor software moves to state 9, continuing the alarm 26. In state 9, two timers are started: the failsafe off timer and the failsafe beep timer. If the operator presses the on/off push-button 22 while the supervisor software is in state 9, the supervisor software will move to state 7 and the power is turned off by sending a SYS_ENABLE signal of a different state to power supply 18. The supervisor software then proceeds directly to state 5, the intermediate off state, where the alarm 26 is silenced by asserting a beep signal of a different state. Upon release of the on/off push-button 22 or the select knob 24, the supervisor software then proceeds to state 1, the normal off state, as described above. On the other hand, if the operator does not press the on/off push-button 22 while the supervisor software is in state 9, the supervisor software moves to state 7 after the failsafe off timer expires (e.g., in 30 seconds) and the patient monitor 10 is powered off by asserting the SYS_ENABLE signal. The alarm 26 continues to sound in state 7 until the failsafe beep timer expires (e.g., in 5 minutes), at which time the supervisor software proceeds to state 5. The supervisor software then proceeds to the resting off state when either the on/off push-button 22 or the select knob 24 is released.

Figure 4:
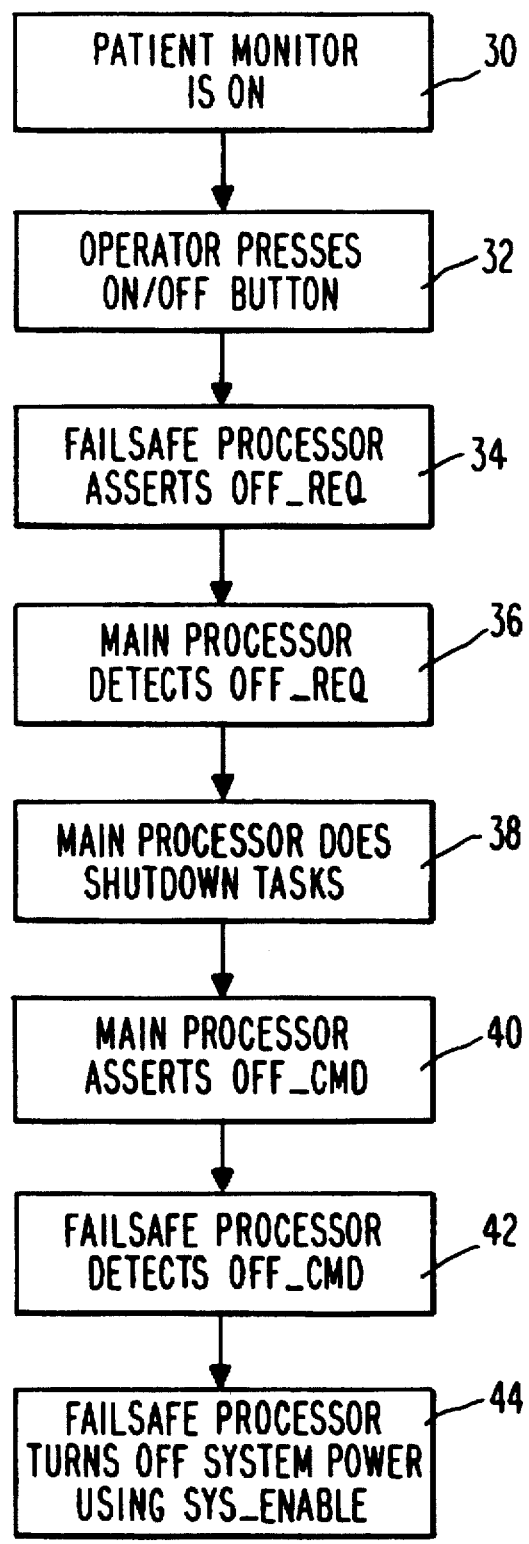
FIG. 4 illustrates a flow diagram of a failsafe power down when the user turns off the patient monitor in accordance with the invention.

FIG. 4 illustrates a flow diagram of a normal failsafe power down when the operator turns off the patient monitor 10 in accordance with the invention. As shown in FIG. 4, with the patient monitor 10 in an on state at step 30, the operator presses on/off push-button 22 to turn off the patient monitor 10 at step 32. The turn off sequence is initiated at step 34 by having the failsafe processor 28 assert OFF_REQ, which is detected at step 36 by main processor 12.

Main processor 12 then performs shutdown tasks at step 38 so as to save data and so as to maintain patient safety. Main processor 12 then asserts the OFF_CMD at step 40, which is detected by the failsafe processor 28 at step 42. Only once these steps are completed is the system power turned off at step 44 by sending an appropriate SYS_ENABLE signal to the power supply 18.

Figure 5:
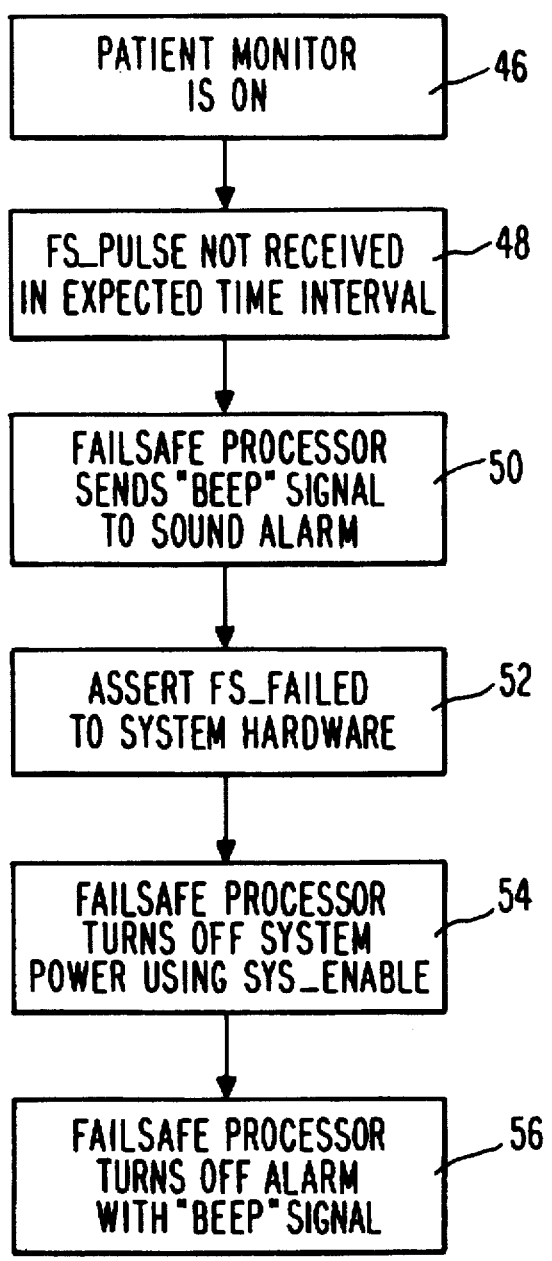
FIG. 5 illustrates a flow diagram of a failsafe power down when an error condition is detected in accordance with the invention.

FIG. 5, on the other hand, illustrates a flow diagram of a failsafe power down when an error condition is detected in accordance with the invention. As shown in FIG. 5, with the patient monitor 10 in an on state at step 46, it is determined by the failsafe processor 28 at step 48 whether the watchdog timer pulse FS_PULSE has been received in the expected time interval. If FS_PULSE is not received in the expected time interval, at step 50 the failsafe processor 28 sends a "BEEP" signal to the alarm 26 to cause it to sound to alert the operator to a system malfunction. The failsafe processor 28 also sends the FS_FAILED signal to the system hardware at step 52 to cause the hardware to power down in a safe manner. The failsafe processor 28 then turns off the system power at step 54 by sending an appropriate SYS_ENABLE signal to power supply 18. Once the system is powered down and the failsafe beep timer expires, the failsafe processor 28 turns off the alarm 26 at step 56 by changing the state of the BEEP signal.

In a preferred embodiment of the invention, the failsafe processor 28 of the invention is implemented in a small one-chip microcontroller which runs off of a backup battery 20 when power supply 18 is off. As will be appreciated by those skilled in the art, the failsafe processor 28 coordinates the functions of turning on/off the patient monitor 10 as well as alerting the operator to unexpected changes of state or malfunctions such as power failure which may cause the patient monitor 10 to switch off for a reason other than deliberate action of the operator. Failsafe processor 28 makes the patient monitor's operation increasingly reliable and failsafe, which is critical when operating a patient monitor 10 which is connected to a critically ill patient.

Although an exemplary embodiment of the invention has been described in detail above, those skilled in the art will readily appreciate that many additional modifications are possible in the exemplary embodiment without materially departing from the novel teachings and advantages of the invention. Accordingly, these and all such modifications are intended to be included within the scope of this invention as defined in the following claims.

What is claimed is:

1. A patient monitor which collects parameter data related to physiological parameters of a patient and displays said parameter data, said monitor comprising:

means for collecting said parameter data;

a display processing means for processing said parameter data and displaying the processed parameter data on said display and for providing watchdog pulses indicating at least whether said collecting means and said parameter processing means are operating properly;

a power supply for selectively providing power to said display, said collecting means, and said parameter processing means upon receipt of a power up or power down signal;

an alarm which sounds upon receipt of an error signal;

an on/off button for selectively turning on/off said patient monitor; and a failsafe supervisor processing means responsive to said on/off button for selectively providing said power up or said power down signals to said power supply and responsive to said watchdog pulses for generating said error signal to sound said alarm when a watchdog pulse is not received by said failsafe supervisor processing means in a predetermined period of time.

2. A patient monitor as in claim 1, further comprising a backup battery for powering said failsafe supervisor processing means at least when said power supply is turned off.

3. A patient monitor as in claim 1, wherein said failsafe supervisor processing means sends an off request to said parameter processing means to cause said parameter processing means to cease its parameter processing in a failsafe manner prior to sending said power down signal to said power supply upon depression of said on/off button while said patient monitor is in an on state.

4. A patient monitor as in claim 1, wherein said failsafe supervisor processing means starts a forced-off timer when said on/off button is depressed while said patient monitor is in an on state, and if said forced-off timer reaches a predetermined count before said on/off button is released, said patient monitor is powered down in a failsafe manner irrespective of the status of any parameter processing by said parameter processing means.

5. A patient monitor as in claim 1, wherein when a watchdog pulse is not received by said failsafe supervisor processing means in said predetermined period of time and said alarm is sounded, said failsafe supervisor processing means starts a failsafe off timer which causes said power down signal to be sent to said power supply after a power down time interval in the event no action is taken by the operator during said power down time interval in response to said alarm.

6. A patient monitor as in claim 1, wherein when a watchdog pulse is not received by said failsafe supervisor processing means in said predetermined period of time and said alarm is sounded, said failsafe supervisor processing means starts an alarm timer which turns off said alarm after an alarm time interval in the event no action is taken by the operator during said alarm time interval to turn off said alarm.

7. A patient monitor as in claim 1, wherein said failsafe supervisor processing means comprises a one-chip microcontroller.

* * * * *

UNITED STATES PATENT AND TRADEMARK OFFICE
CERTIFICATE OF CORRECTION

PATENT NO. : 5,746,203
DATED : May 5, 1998
INVENTOR(S) : Rush W. Hood, Jr.

It is certified that error appears in the above-identified patent and that said Letters Patent is hereby corrected as shown below:

Col. 6, line 58, change "$OFF_{13}CMD$" to -OFF__CMD-.

Signed and Sealed this

Twenty-ninth Day of December, 1998

Attest:

BRUCE LEHMAN

Attesting Officer

Commissioner of Patents and Trademarks